(12) United States Patent
Wardlaw

(10) Patent No.: US 7,182,742 B2
(45) Date of Patent: Feb. 27, 2007

(54) FRACTURE BRACE

(75) Inventor: Douglas Wardlaw, Stonehaven (GB)

(73) Assignee: Grampian Health Board, Aberdeen (GB)

( * ) Notice: Subject to any disclaimer, the term of this patent is extended or adjusted under 35 U.S.C. 154(b) by 480 days.

(21) Appl. No.: 10/168,029

(22) PCT Filed: Dec. 18, 2000

(86) PCT No.: PCT/GB00/04747

§ 371 (c)(1), (2), (4) Date: Sep. 30, 2002

(87) PCT Pub. No.: WO01/43671

PCT Pub. Date: Jun. 21, 2001

(65) Prior Publication Data

US 2003/0093020 A1    May 15, 2003

(30) Foreign Application Priority Data

Dec. 17, 1999  (GB) .................................. 9929944.8

(51) Int. Cl.
*A61F 5/00* (2006.01)
*A61F 5/37* (2006.01)

(52) U.S. Cl. .............................. 602/21; 602/5; 602/20; 128/877; 128/878

(58) Field of Classification Search ................ 602/20, 602/26, 5, 6, 12, 16, 21, 23, 27; 128/877, 128/878, 881, 892; 606/53, 54, 57
See application file for complete search history.

(56) References Cited

U.S. PATENT DOCUMENTS

| | | | |
|---|---|---|---|
| 3,299,888 A | | 1/1967 | Muckinhaupt |
| 4,662,364 A | | 5/1987 | Viegas et al. |
| 4,796,611 A | * | 1/1989 | Wardlaw ..................... 602/12 |
| 4,803,975 A | | 2/1989 | Meyers |
| 4,943,293 A | | 7/1990 | Lee, Jr. |
| 5,312,322 A | * | 5/1994 | Santana ....................... 602/20 |
| 5,383,844 A | * | 1/1995 | Munoz et al. ................ 602/20 |
| 6,063,087 A | * | 5/2000 | Agee et al. ................... 606/55 |

FOREIGN PATENT DOCUMENTS

| | | |
|---|---|---|
| EP | 0255388 | 2/1988 |
| GB | 2193102 | 2/1988 |
| WO | WO 91 05525 | 5/1991 |

* cited by examiner

*Primary Examiner*—Justine R. Yu
*Assistant Examiner*—Annette Dixon
(74) *Attorney, Agent, or Firm*—Drinker Biddle & Reath LLP

(57) ABSTRACT

An orthopaedic brace apparatus for the treatment of fractures is described. The brace comprises two portions (2,3) joined together by a strap (4). The first portion (2) comprises at least one preformed pad and the second portion (3) comprises at least two preformed pads (5, 6) joined together by resilient material (7). The resilient material is elastically deformable and the preformed pads are formed from a material that resists slippage such that the apparatus provides gentle compression on the fracture.

22 Claims, 10 Drawing Sheets

FRACTURE BRACE

CROSS REFERENCE TO RELATED APPLICATIONS

This application is the US National Phase Application of PCT International Application No PCT/GB00/04747 filed Dec. 18, 2000.

FIELD OF THE INVENTION

This invention relates to the treatment of fractures, and it relates especially, although not exclusively, to apparatus for effecting such treatments as are applicable to fractures of long bones such as the radius.

DESCRIPTION OF RELATED ART

Traditional methods of treating simple fractures include fracture bracing. A previous fracture brace is detailed in patent numbers GB 2 193 102 and EP 0 255 388. Such a prior art fracture brace is a rigid brace, which comprises two main parts, conjoined together by two elasticated VELCRO (i.e. hook and loop) fastener straps (VELCRO is a registered trademark of Velcro Industries B.V. for hook and loop fasteners). The main part covers the dorso-radial surfaces of the forearm from the level of the radio-carpal joint and radial styloid for approximately two thirds of the forearm. At either end of the brace, there are two areas of high loading of a specified size, which are raised by approximately 5 millimeters. The second portion of the brace is applied to the antero-ulnar aspect of the forearm and has a similar raised area of a specified size.

Clinical trials carried out in Aberdeen showed that the concept of the brace was correct. Unfortunately when multicentre clinical trials were carried out, optimum results were not achieved. In general existing fracture bracing techniques may allow earlier mobilisation of the fracture but they fail to maintain the fracture position adequately enough to allow a significant long term advantage.

The standard treatment for Colles Fractures throughout the world remains the use of a so-called Colles Plaster of Paris cast. Usually one is applied at the time of fracture reduction and then changed after ten days to two weeks to a definitive cast for a further four weeks or so. This immobilises the wrist and leaves a very stiff wrist which takes several months to recover. Also, this method of treatment is sometimes not successful in maintaining the fracture position and leaves significant long-term deformity of the wrist. This fracture occurs most commonly in elderly people and during the period of cast treatment and subsequent rehabilitation they have very little proper use of the hand.

Many of them live on their own and as a result their ability to look after themselves is significantly impaired in the short term. The fracture brace described above has shown that by allowing earlier function, the pinch-grip, that is the ability to hold objects between the finger and thumb, and grip strength return much earlier than would otherwise happen and this function in itself is very useful. However, the brace as designed does not in a multi-centre trial appear to be able to maintain the fracture position any better than a standard cast and so the long term results were similar.

Kirschner wires (K-wires) are often used in the more comminuted fracture in an attempt to maintain the fracture position better. However, they tend to hold the fragments poorly and very often the fracture re-displaces despite their use. Clinical studies have not shown the long-term results to be any better than Colles cast treatment and the patient's wrist also needs to be immobilized in a cast during this form of treatment. In addition, pin track infection of the K-wire sometimes occurs.

A further alternative form of treatment is to use external fixators whereby pins are applied into the second metacarpal bone and into the radius proximal to the fracture.

The fracture is reduced and the external fixator is applied holding the fracture fragments in a distracted, reduced, position. Unfortunately, this immobilises the wrist and leaves a very stiff wrist which again requires a long period of rehabilitation. External fixation has also been applied to the less comminuted fractures where there is one fairly large distal fragment through which pins can be inserted and this is done along with pins in the radius proximal to the fracture. The external fixator is then able to hold the fracture reduced and allow the wrist to move. However, the external fixator in this position is an extremely cumbersome thing and doesn't allow patients to put on normal clothing and also gets in the way when sleeping and carrying out activities. It is not applicable to many fractures.

Inevitably, pin tract infection will occur in some cases.

BRIEF SUMMARY OF THE INVENTION

An object of the present invention is to provide sustained fracture reduction throughout treatment. By maintaining fracture loading and where a fracture is comminuted using K-wires passed into the fracture fragments and attached to the distal loading area of the brace the fracture is maintained in a desired location. Thus the present invention also combines the use of K-wires with traditional fracture bracing to treat those more complicated fractures.

The present invention can thus result in an enhanced fracture reduction and correct alignment. Therefore, the present invention can result in improved stability of fractured bones and/or mobility of joints. Hence, there can be a decreased incidence of deformity and/or morbidity as bones and joints are allowed free movement in a stabilised manner.

The present invention optimises the effect of using an orthopaedic brace in that it enhances fracture loading throughout the duration of the period of treatment.

It is thought that an advantage of the present invention is the mechanism employed in maintaining fracture loading. In contrast to the aforementioned rigid brace, the present invention involves the substitution of the rigid material of the brace by one or two resilient polypropylene sections. As swelling at the fracture location decreases, the previous rigid braces were unable to maintain fracture loading adequately. The resilient material in the present invention stores energy when it is deformed, thereby releasing energy as it returns to its initial shape. The result of this feature of the present invention is to maintain pressure on the fracture area. Alternatively a rigid material 7" may be used which is spring-loaded at either end by springs 24 such that the springs 24 are deformed and energy is released as the swelling goes down and the springs 24 return to their initial shape (see FIGS. 9A and 9B). In this way again, pressure is maintained on the fracture area.

In a preferred embodiment, the present invention comprises an almost constant loading force at three points.

The polypropylene or similar material must be resilient in that it must have an elastic memory such that when deformed it will return to its original shape. It may be shaped to ensure that it deforms at either end, or may be mobile at one end allowing it to slide in a groove as it is deformed. The use of this mechanism to maintain fracture loading enables the loading to be maintained more uniformly as the fracture swelling is reduced.

The present invention also comprises a further means of enhancing fracture reduction. The present invention allows the use of metal pins, or K-wires, to be inserted percutaneously into the distal fracture fragments in more comminuted fractures. Further, the use of hypoallergenic adhesive on the skin surface of the proximal loaded area of the present invention to maintain its position, will enhance the effect of the invention.

BRIEF DESCRIPTION OF THE SEVERAL VIEWS OF THE DRAWINGS

In order that the invention may be clearly understood and readily carried into effect, one embodiment thereof will now be described, by way of example only, with reference to the accompanying drawings, in which.

The locking mechanism which prevents migration of the pins is also depicted.

Figure 7:
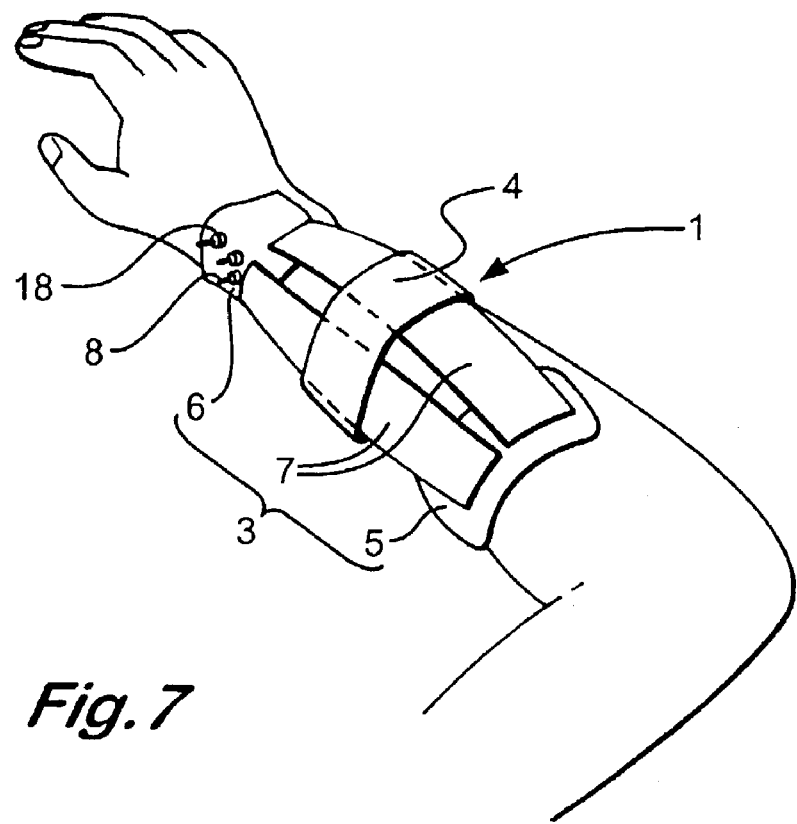

FIG. 7 shows the dorso-radial portion of the brace which is held in position by the velcro strap and distal loading area with K-wires and locking mechanism in place on the arm.

Figure 1:
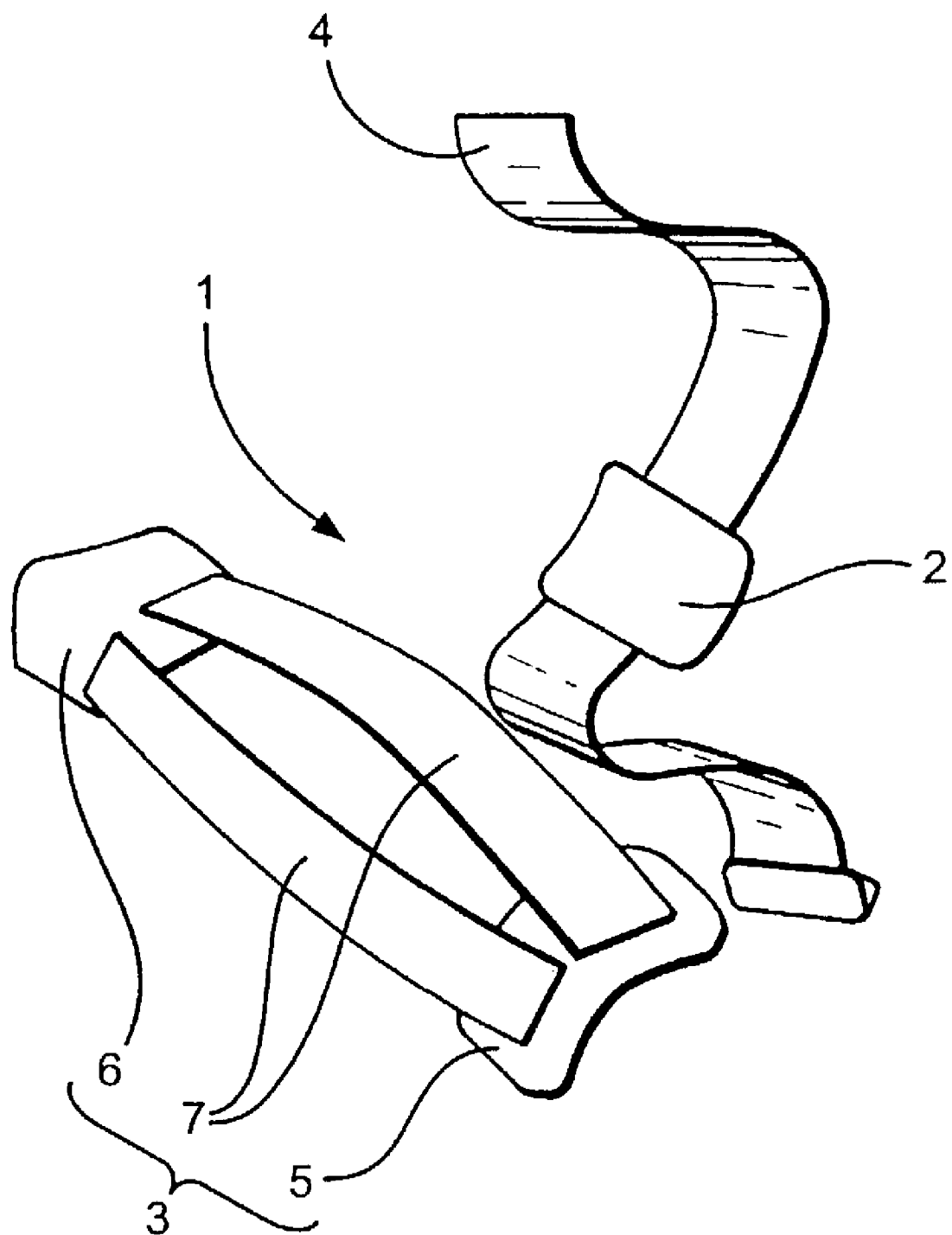
FIG. 1 shows the revised brace which comprises a dorsoradial portion and an antero-ulnar portion and an elasticated velcro strap in open plan view.
Figure 2:
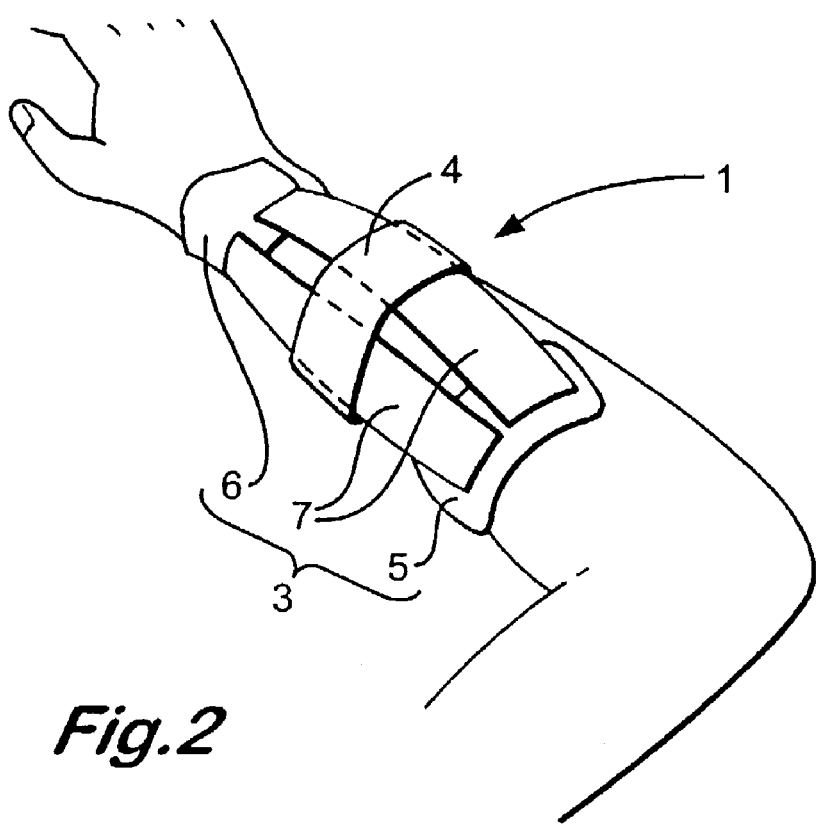
FIG. 2 shows the dorso-radial portion of the revised brace with the velcro strap in position, from a perspective view.
Figure 3:
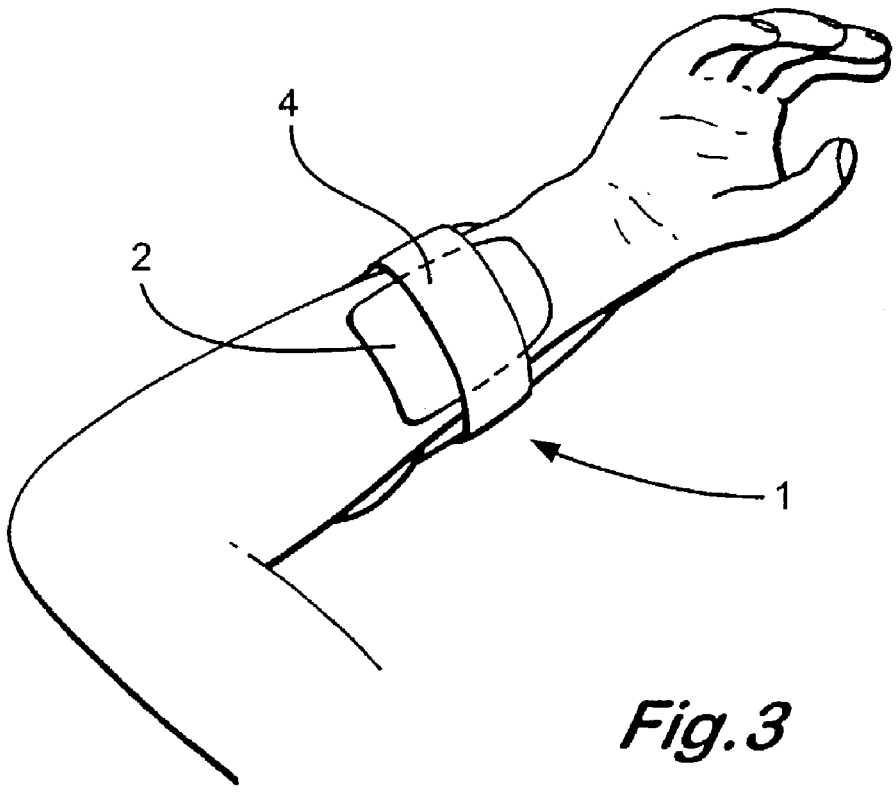
FIG. 3 shows the antero-ulnar portion of the revised brace with the velcro strap in position, from a perspective view.
Figure 8:
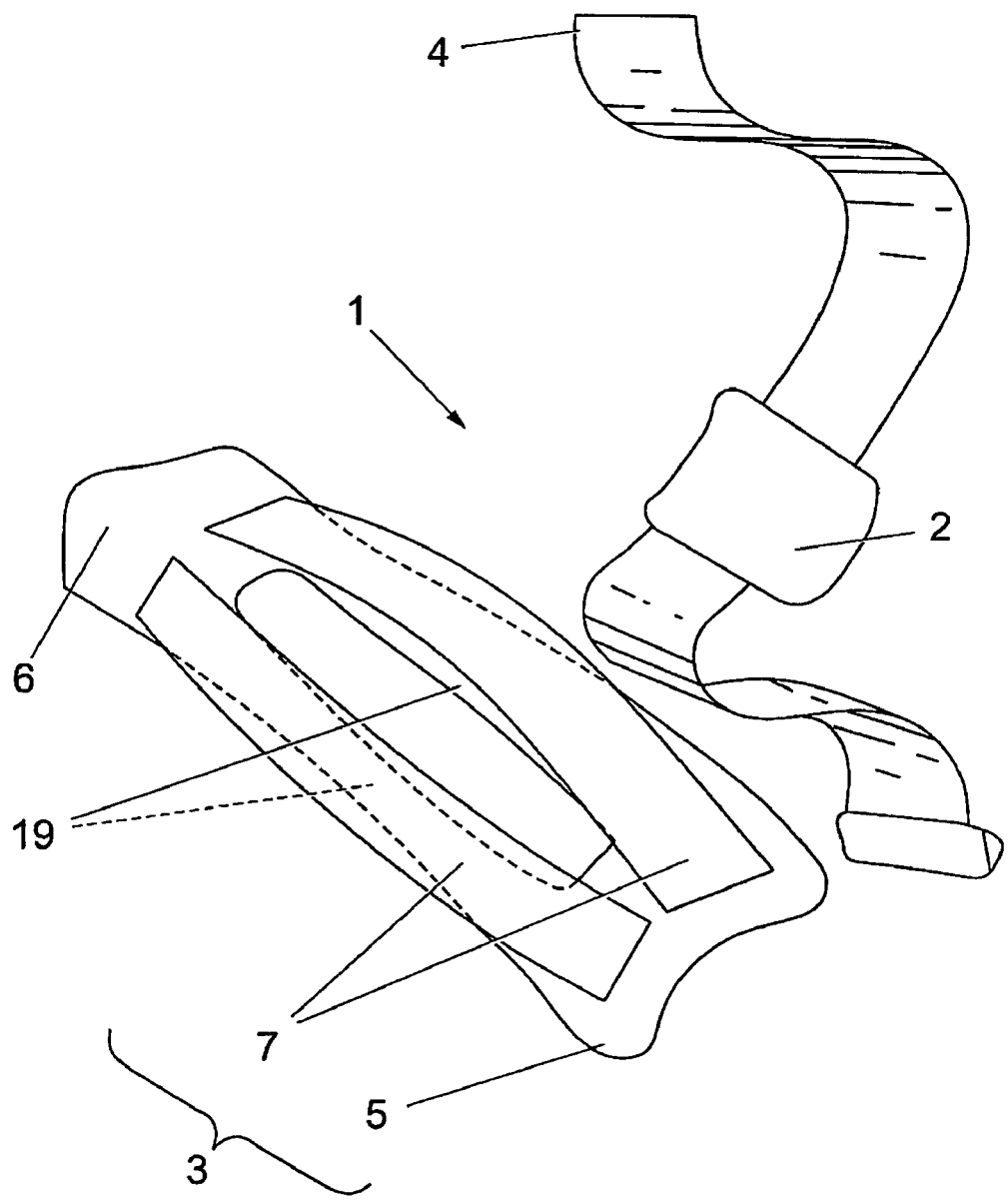

FIG. 8 shows a modified fracture brace, similar to the embodiment of FIGS. 1 to 3, also including two rigid struts between the two load areas.

Figure 9A:
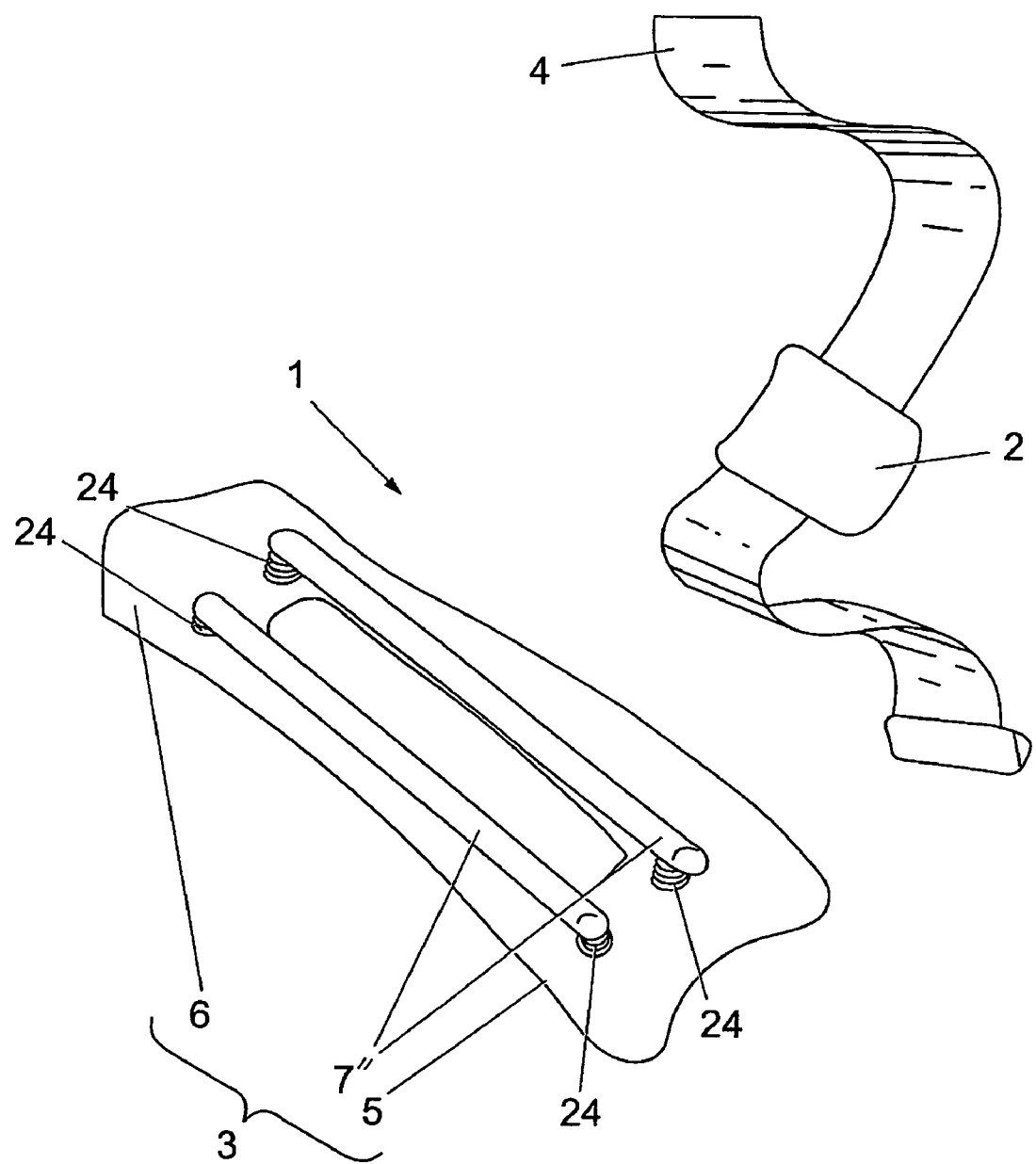
Figure 9B:
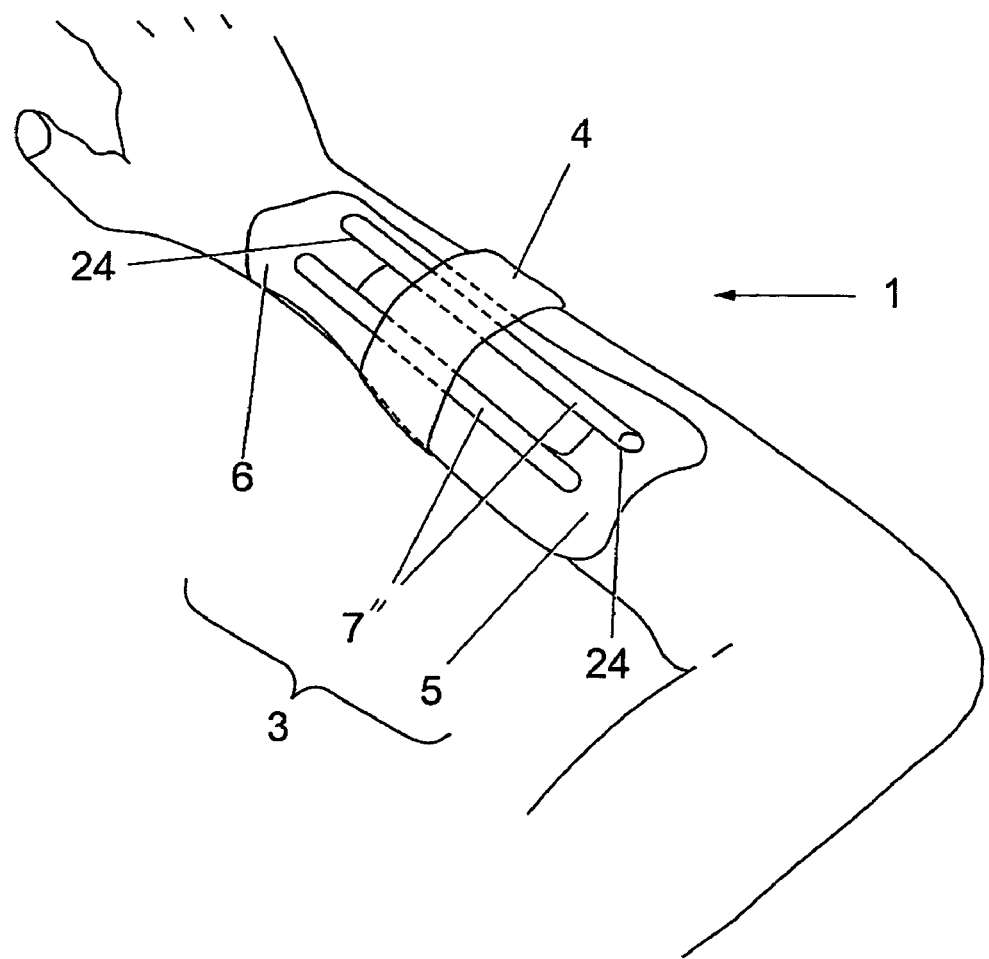

FIGS. 9A and 9B show a further modified fracture brace, including elongate members that comprise a rigid material that is spring loaded at either end.

Figures 10A, 10B, 10C:
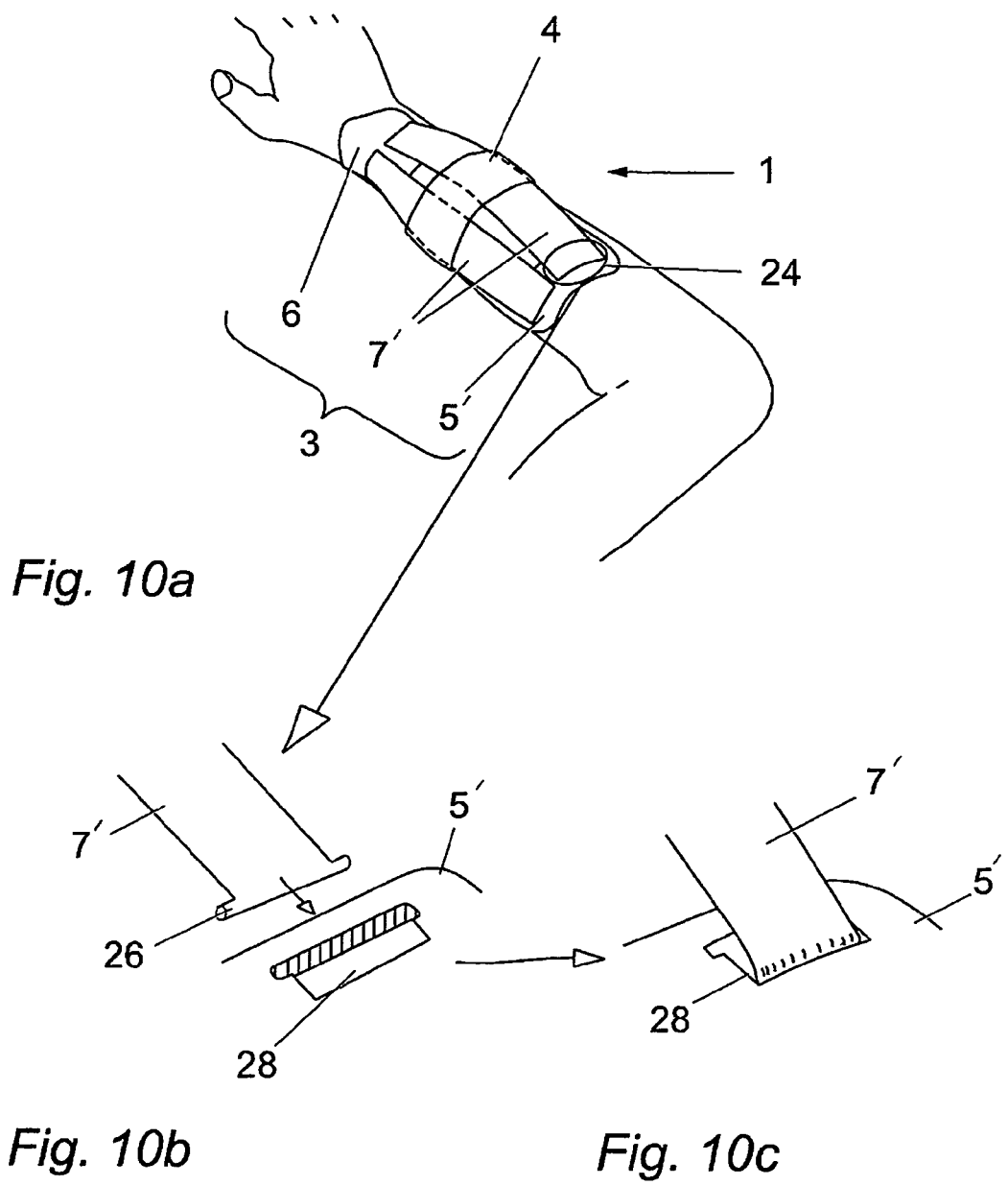

FIGS. 10A to 10C show a further modified fracture brace, similar to the embodiment of FIGS. 1 to 3, but with struts that are mobile at one end and which slide in a groove as they are deformed.

Figure 6:
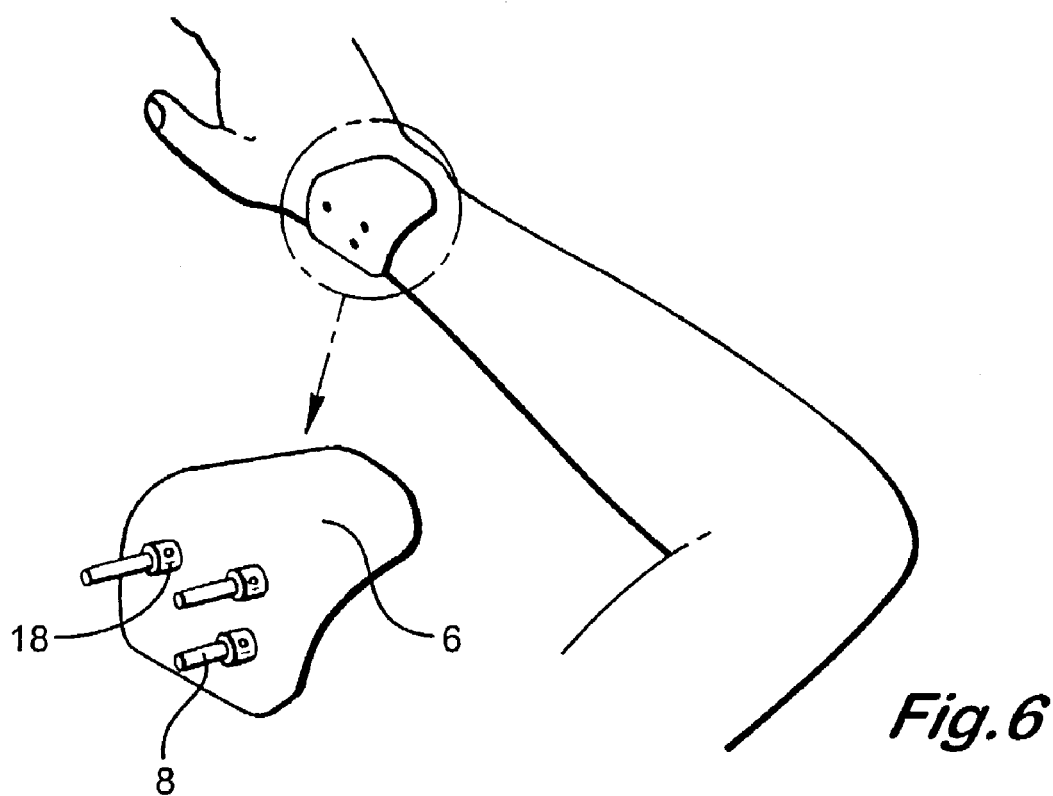
FIG. 6 shows how when the jig is removed, a specially designed distal loading area with holes in it in exactly the same position as the jig, can be fitted over the K-wires.
Figure 11:
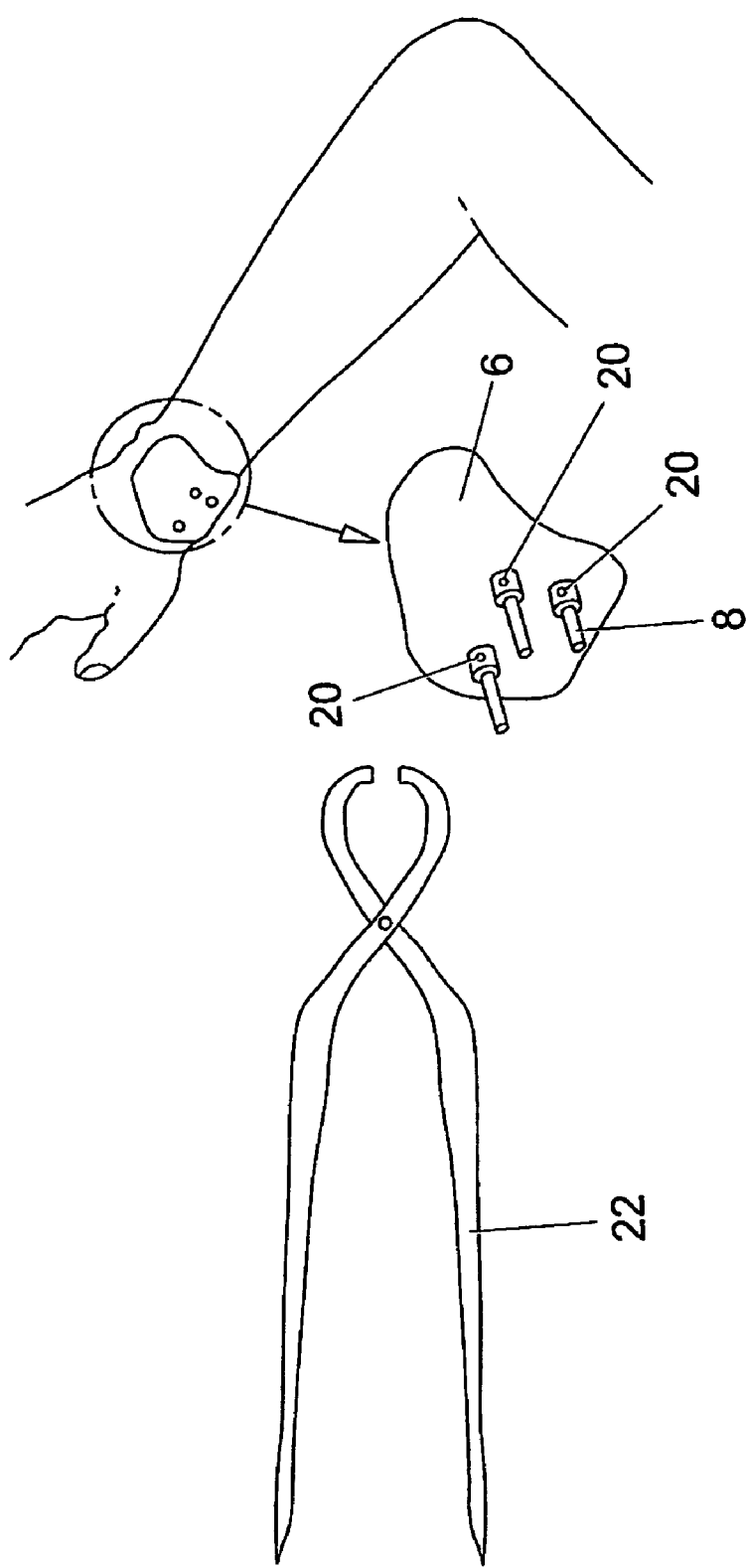
Figure 12:
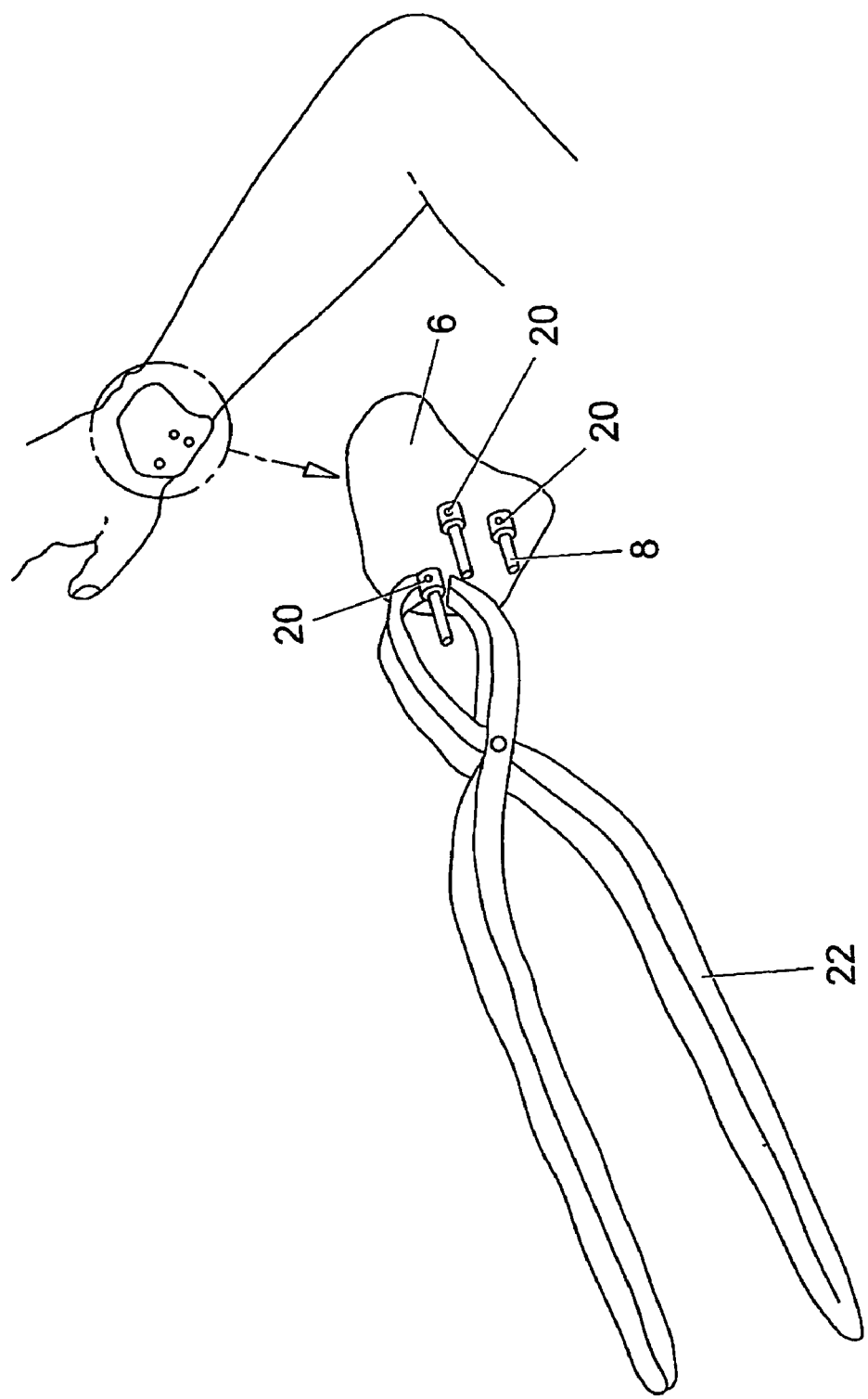

FIGS. 11 and 12 show a further modified fracture brace, similar to the embodiment of FIGS. 6 and 7, but having a crimping mechanism to fix pins to a distal loading area.

DETAILED DESCRIPTION OF THE INVENTION

Referring now to FIG. 1, the brace 1 consists of two main parts, an antero-ulnar portion 2, and a dorso-radial portion 3, joined together in use by an elasticated VELCRO (i.e. hook and loop fastener) strap 4.

The dorso-radial portion, which is intended to cover the dorso-radial aspect of the forearm, has two load areas, a proximal load area 5, and a distal load area 6, which areas are joined by two slightly curved struts of the same polypropylene material 7. FIG. 8 shows a modified embodiment, in which, in addition, two rigid struts 19 ensure a fixed distance between the two loaded areas when the curved polypropylene material has deformed.

The polypropylene or similar material must have a memory such that when deformed it will return to its original shape. It may be shaped to ensure that it deforms at either end, Alternatively, each polypropylene strut 7' may be mobile at one end 26, allowing it to slide in a groove 28 as it is deformed, as shown in the embodiment of FIGS. 10A to 10C.

The antero-ulnar portion 2 also has a centrally positioned load area, which is provided with a single elasticated strap 4 attached to it.

In use the fracture is reduced and the brace 1 applied immediately after the injury, (See FIGS. 2 and 3). The main part covers the dorso-radial surfaces of the forearm from the level of the radio-carpal joint and radial syloid proximally for two thirds of the forearm approximately. At either end of the brace, there are two areas of high loading 5 & 6, of a specified size, FIG. 2. The smaller portion of the brace 1 is applied to the antero-ulnar aspect of the forearm, FIG. 3.

Following this method, the fracture is reduced, and the dorso-radial portion 3 is positioned (See FIG. 2), while the antero-ulnar portion 2 is positioned (See FIG. 3), the strap 4 tightened and tensioned according to a colour code.

When the brace is tensioned the resilient struts of polypropylene 7 will tend to straighten out. Energy is thus stored in both the tensioned straps 4 and the deformed polypropylene 7, which acts like a spring.

Thus the mechanism for maintaining the loading on the fracture as the swelling goes down is significantly improved because the device attempts to maintain a degree of compression between the two load areas of the dorso-radial portion 3.

Figure 4:
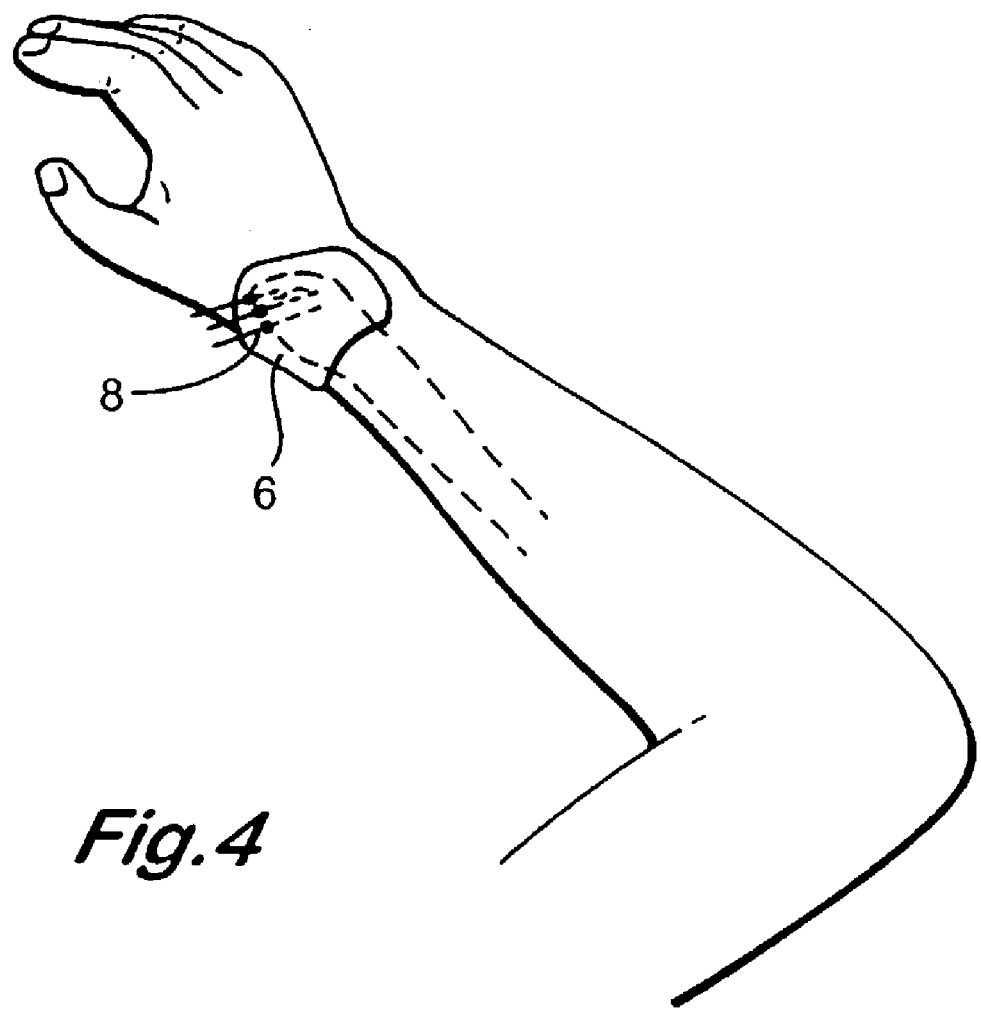
FIGS. 4 and 5 show the insertion of K-wires into distal fracture fragments by the use of a jig.
Figure 5:
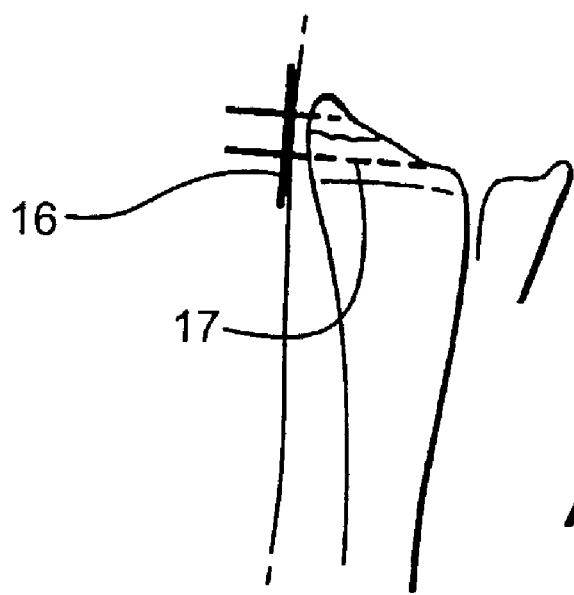

A further embodiment of the invention involves the use of metal pins or K-wires 8 which are to be inserted percutaneously into the distal fracture fragments in the more comminuted fractures (See FIG. 5) by passing through holes in the distal loading area, (See FIG. 4). This combines two recognised techniques to help maintain fracture reduction, namely the use of percutaneous pins or K-wires 8 and a functional brace 1.

The pins or K-wires 8 are inserted as follows. The fracture is reduced in the usual fashion. The metal pins or K-wires 8 are inserted into the distal fracture fragments using a jig 16, (See FIGS. 4 and 5). The jig 16 spaces the wires 17 and directs them such that they enter the fracture fragments appropriately. When the jig 16 is removed, a specially designed distal loading area 6 with holes on it in exactly the same position as the jig, is fitted over them, (See FIGS. 6 and 7). The pins 8 are then fixed to the distal loading area 6 by lock nuts 18 or a crimping mechanism (20, 22) as shown in FIGS. 11 and 12, to ensure that no migration of the pins occurs. The full brace 1 is then positioned and tensioned as above, (See FIG. 7).

The invention resides therefore in an orthopaedic brace, and to a method for applying the same to an injured limb as hereinbefore set forth.

The invention claimed is:

1. A fracture brace comprising at least two portions conjoinable by a strap, wherein a first portion comprises at least one preformed pad and a second portion comprises at least two preformed pads conjoined by at least one elongate member having resilient means, said resilient means being elastically deformable when fitted about a fracture and wherein each pad comprises a material of a friction value such that the pads are adapted to resist slippage, thereby providing a gentle compression on the fracture.

2. A fracture brace according to claim 1, wherein the elongate member comprises a resilient material.

3. A fracture brace according to claim 2, wherein the elongate member is shaped to deform at at least one end.

4. A fracture brace according to claim 2, wherein the elongate member is mobile at one end and is adapted to slide in a groove as it is deformed.

5. A fracture brace according to claim 1, wherein the elongate member comprises a rigid material and the resilient means comprises a spring provided at either end of the elongate member.

6. A fracture brace according to claim 1 adapted for use on a limb.

7. A fracture brace according to claim 1 wherein the elongate member conjoining the preformed pads comprises polypropylene.

8. A fracture brace according to claim 1, wherein at least two elongate members are provided.

9. A fracture brace according to claim 1, wherein the preformed pads each comprise a high-friction, adhesive material adapted to increase the friction pressure at a brace/skin interface, when the brace is applied to a user's skin.

10. A fracture brace according to claim 1, wherein the two portions when formed about a fractured limb provide at least three areas of constant loading at the point of contact of the pads and wherein the brace is adapted to be held in position by an elasticized strap which applies pressure to the resilient material of the brace resulting in a longitudinally contracting force.

11. A fracture brace according to claim 1, wherein at least one pad comprises at least one hole to accommodate a respective fixing device; the fixing device being selected from the group consisting of pins and k-wires.

12. A fracture brace according to claim 1, adapted to treat bone fractures of the human body.

13. A fracture brace comprising at least two portions conjoinable by a strap, wherein a first portion comprises at least one preformed pad and a second portion comprises at least two preformed pads conjoined by at least one elongate member having resilient means, said resilient means being elastically deformable when fitted about a fracture, wherein each pad comprises a material of a friction value such that the pads are adapted to resist slippage, and wherein at least one rigid strut ensures a fixed distance between the at least two preformed pads.

14. A method of treating a fracture, comprising the steps of:
   moving the fracture fragments into a desired location;
   applying a first portion of a brace to the fracture, the first portion having at least one preformed pad;
   applying a second portion of the brace to the fracture, the second portion having at least two preformed pads conjoined by at least one elongate member having a resilient means that is elastically deformable;
   wherein each pad comprises a material of a friction value such that the pads are adapted to resist slippage; and
   tensioning a strap conjoining the first and second portions so that the at least one elongate member is deformed, thereby compressing the fracture.

15. A method as claimed in claim 14, further including the steps of inserting at least one bone fixing device into a bone on at least one side of the fracture, and coupling the at least one bone fixing device to either of the pads on the second portion; the bone fixing device being selected from the group consisting of pins and k-wires.

16. A method as claimed in claim 15, wherein a jig is used in the insertion of the or each bone fixing device.

17. A method as claimed in claim 15, wherein the or each bone fixing device is coupled to its pad by a respective nut.

18. A method as claimed in claim 15, wherein the or each bone fixing device is coupled to its pad by a crimping mechanism.

19. A method as claimed in claim 14, wherein the fracture is on a limb and the pads of the first and second portions are applied to opposite surfaces of the limb.

20. A method as claimed in claim 14, wherein the first portion has one pad which is located towards the centre of the brace, and the second portion has two pads located substantially at opposite ends of the brace.

21. A method as claimed in claim 14, wherein one of the preformed pads is positioned on top of the fracture site to maintain the fracture in the desired location.

22. A method as claimed in claim 14, wherein the second portion of the brace is applied to the fracture before the first portion of the brace is applied to the fracture.

* * * * *